US00PP36440P2

(12) United States Plant Patent
Rupp

(10) Patent No.: US PP36,440 P2
(45) Date of Patent: Feb. 11, 2025

(54) ***DIANTHUS* PLANT NAMED 'KLEDG23495'**

(50) Latin Name: ***Dianthus caryophyllus* L.**
Varietal Denomination: KLEDG23495

(71) Applicant: KLEMM + SOHN GMBH & CO. KG, Stuttgart (DE)

(72) Inventor: Judith Rupp, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/657,482

(22) Filed: May 7, 2024

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

(56) References Cited

PUBLICATIONS

Selecta *Dianthus* Early Spring Crops catalog 2023/2024 (Year: 2023).*

* cited by examiner

*Primary Examiner* — Keith O. Robinson
(74) *Attorney, Agent, or Firm* — Weatherly IP Solutions , LLC; James M. Weatherly; Karen P. Bechtold

(57) ABSTRACT

A new *Dianthus* plant designated 'KLEDG23495' particularly distinguished by double, salmon colored flowers that change in appearance based on light intensity and an upright plant form, is disclosed.

2 Drawing Sheets

*Dianthus caryophyllus* L.
Variety denominations: 'KLEDG23495'.

BACKGROUND

The present invention comprises a new and distinct variety of *Dianthus*, botanically known as *Dianthus caryophyllus* L., and hereinafter referred to by the variety name 'KLEDG23495'. 'KLEDG23495' originated from a cross pollination from the proprietary female parent 'DSS-2011-0111' (unpatented) and the proprietary male parent 'DSS-2016-0060' (unpatented) in 2017 between May and August in Stuttgart, Germany.

'KLEDG23495' was selected and first vegetatively propagated in June 2018 by vegetative stem cuttings in Stuttgart, Germany. 'KLEDG23495' was found to reproduce true to type in successive generations of asexual propagation in Stuttgart, Germany via vegetative stem cuttings.

SUMMARY

The following are the most outstanding and distinguishing characteristics of 'KLEDG23495' when grown under normal horticultural practices in Stuttgart, Germany.

1. Double, salmon colored flowers that change in appearance based on light intensity;
2. Upright plant form.

DESCRIPTION OF THE PHOTOGRAPHS

These new *Dianthus* plants are illustrated by the accompanying photographs taken in a greenhouse in Stuttgart, Germany. The colors shown are as true as can be reasonably obtained by conventional photographic procedures.

DESCRIPTION OF THE PLANT

Figure 1:
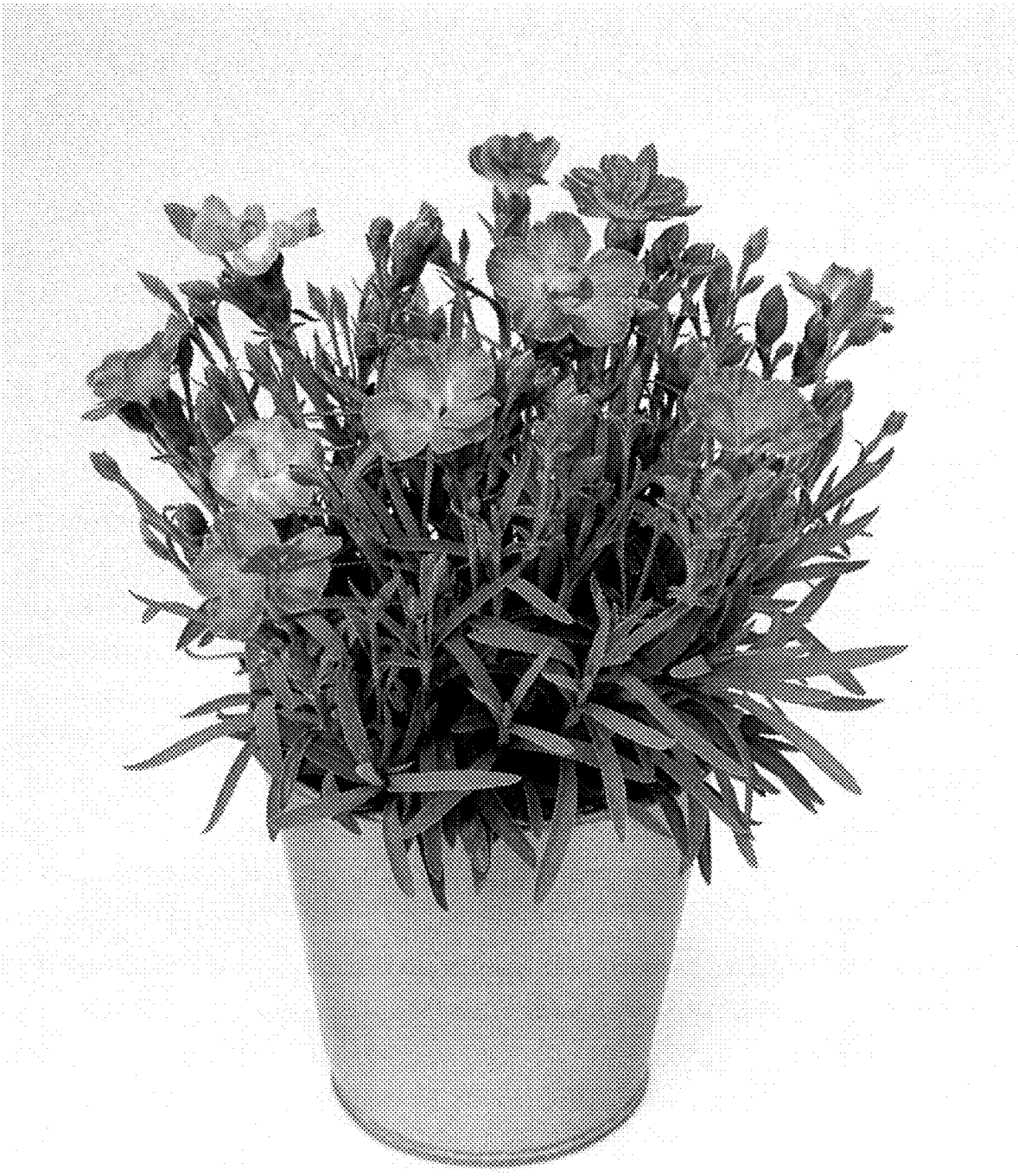
FIG. 1 is a photo of a whole plant of the new *Dianthus* plant at 12 weeks old showing the foliage, buds and flower of a 12-week-old plant taken in April 2022.
Figure 2:
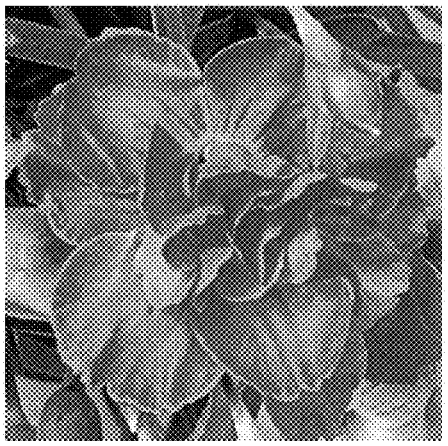
FIG. 2 is a photo of flower of the new *Dianthus* at six months old under low light conditions in a greenhouse in Stuttgart, Germany in April 2020.
Figure 3:
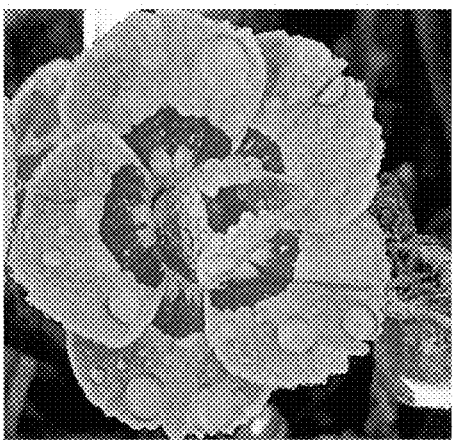
FIG. 3 is a photo of flower of the new *Dianthus* plant at two months old under high light conditions in a greenhouse in Stuttgart, Germany in August 2020.

The following detailed descriptions set forth the distinctive characteristics of 'KLEDG23495'. The data which define these characteristics were collected from asexual reproductions carried out in Stuttgart, Germany. Data was collected in April 2024 on 6-month old plants grown in a plastic greenhouse. Color references are to The R.H.S. Colour Chart of The Royal Horticultural Society of London (R.H.S.), 5$^{th}$ edition (2007).

Classification:
*Family*.—Caryophyllaceae.
*Botanical*.—*Dianthus caryophyllus* L.
*Common*.—Pot carnation.
*Designation*.—'KLEDG23495'.

Parentage:
*Female parent*.—'DSS-2011-0111'.
*Male parent*.—'DSS-2016-0060'.

Plant:
*Propagation type*.—Vegetative cuttings via stem.
*Time to produce a rooted young plant*.—28 days.
*Root description*.—Fine; roots, color is white (RHS 155D).

*Rooting habit shape*.—Lanceolate.
*Plant form*.—Upright.
*Plant height*.—18.0 cm.
*Plant diameter or spread*.—23.0 cm.

Lateral branches/stems:
*Shape of the branch in cross-section*.—Circular.
*Hollowness of the branch*.—Absent.
*Length*.—15.0 cm.
*Diameter*.—5.0 cm.
*Internode length*.—2.0 cm to 2.5 cm.
*Internode thickness*.—Medium.
*Internode quantity per branch*.—4 to 5.
*Number of internodes per branch/stem*.—4 to 5.
*Node length*.—0.4 cm.
*Node diameter*.—0.3 cm.
*Texture*.—Smooth.
*Color*.—RHS139D.
*Flower clustering on the lateral branch*.—None.

Foliage:
*Arrangement*.—Opposite.
*Length*.—4.0 to 5.0 cm.
*Width*.—0.4 cm.
*Shape*.—Linear.
*Apex*.—Narrowly acute.
*Base*.—Round.
*Margin*.—Entire.
*Texture* (*both upper and lower surfaces*).—Smooth.
*Cross-section of the leaf*.—Weakly concave.
*Curvature of the leaf*.—Absent.
*Glaucosity of the leaf*.—Weak.
*Leaf color* (*both immature and mature*).—Immature: Upper surface: RHS 137B. Lower surface: RHS 137D. Mature: Upper surface: RHS 137B. Lower surface: RHS 137D.
*Venation pattern*.—Absent.

Flowers:
*Flower type and habit*.—Double.
*Fragrance*.—Present.
*Position of the flowers compared to the foliage of the plant*.—Moderately above.
*Profile of both the upper and lower part in the lateral view*.—Flat convex.
*Diameter of the flower*.—3.5 cm to 4.0 cm.
*Natural flowering season*.—Spring to autumn.
*Number of flowers per spray*.—2 to 3.
*Flower longevity on the plant*.—20 days.

Buds:
*Length*.—1.8 cm.
*Diameter*.—0.7 cm.
*Shape*.—Oblong.
*Color*.—Upper part is RHS 138A, Lower part 144B.
*Extrusion of the styles at the bud stage*.—Absent.

Corolla:
*Quantity of petals and arrangement*.—15 petals and arranged in several whorls.
*Corolla height*.—1.8 cm.
*Petal length*.—3.4 cm.
*Petal width*.—1.9 cm.
*Petal shape*.—Spoon shaped.
*Petal apex*.—Obtuse.
*Petal base*.—Acute.
*Petal margin*.—Inserted.
*Depth of petal margin*.—Shallow.
*Petal texture* (*both upper and lower surfaces*).—Smooth.
*Petal color*.—Immature: Upper surface: RHS 50A with RHS 52A macule under low light, RHS 55A with RHS 55C macule under high light conditions. Lower surface: RHS 52D. Mature: Upper surface: RHS 52B with RHS 52A macule under low light, RHS 55A with RHS 55C macule under high light conditions. Lower surface: RHS 52D.
*Macule*.—Present.
*Macule size*.—Medium.

Calyx:
*Quantity of sepals and arrangement*.—Composed of 4 sepals.
*Longitudinal axis of the lobes of the calyx*.—Straight.
*Shape*.—Cylindrical.
*Calyx height*.—2.0 cm.
*Calyx diameter* (*at the apex*).—0.7 cm.
*Sepal texture* (*both upper and lower surfaces*).—Smooth.
*Sepal color*.—Upper surface: RHS 139B. Lower surface: RHS 139C.
*Position of the outer lobes of the epicalyx in relation to the calyx*.—Adpressed.
*Apex shape of the outer lobes of the epicalyx*.—Medium acuminate.
*Tip length of the outer lobes of the epicalyx*.—0.2 cm.
*Apex shape of the inner lobes of the epicalyx*.—Short acuminate.
*Tip length of the inner lobes of the epicalyx*.—0.2 cm.

Peduncles:
*Length*.—2.0 cm.
*Diameter*.—0.15 cm.
*Strength*.—Medium.
*Texture*.—Smooth.
*Color*.—RHS 139B.

Reproductive organs:
*Stamens*.—None.
*Pistils*.—Quantity per flower: 2. Length: 1.1 cm. Diameter: 0.1 cm. Stigma: Color: RHS 75D. Shape: Filamentous. Length: 0.2 cm. Diameter: Less than 0.1 cm. Style: Number of styles observed: 2. Style shoulder: Absent. Color: RHS 155A. Length: 0.9 cm. Diameter: 0.1 cm. Ovary: Shape: Obovate. Texture: Smooth. Color: RHS 145B. Width: 0.6 cm.

Seeds: Yes.
*Color*.—RHS 200B to RHS 202A (Brown-black).
*Size*.—0.2 cm to 0.3 cm.
*Shape*.—Drop shaped.

Disease and insect resistance: No particular disease or insect resistance observed.

COMPARISON WITH PARENTAL LINES AND KNOWN VARIETY

'KLEDG23495' is distinguished from the parental lines as described in Table 1.

TABLE 1

| Comparison with Parental Lines | | | |
|---|---|---|---|
| Characteristic | 'KLEDG23495' | Female Parent | Male Parent |
| Flower filling | Double | Double | Single |
| Flower color | Salmon | Purple, pink border | Soft cream, red purple ring |

'KLEDG23495' can be compared to the commercial *Dianthus* variety 'KLEDG20339' (U.S. Plant Pat. No. 34,855). Differences between the varieties are described in Table 2.

TABLE 2

| Comparison with Similar Variety | | |
|---|---|---|
| Characteristic | 'KLEDG23495' | 'KLEDG20339' |
| Flower color | Salmon | Light cream |

I claim:

1. A new and distinct cultivar of *Dianthus* Plant Named 'KLEDG23495' as illustrated and described herein.

* * * * *